United States Patent [19]

King et al.

[11] Patent Number: 4,615,007
[45] Date of Patent: Sep. 30, 1986

[54] AUDIOLOGIC TESTING METHOD AND APPARATUS WITH COMPENSATING MEANS FOR SOUNDWAVE ATTENUATION THROUGH A TRANSMITTING MEDIUM

[75] Inventors: James T. King; Charles W. Beatty, Jr., both of Longview, Tex.

[73] Assignee: Audiometrics, Inc., Longview, Tex.

[21] Appl. No.: 651,118

[22] Filed: Sep. 14, 1984

[51] Int. Cl.$^4$ .................. G06F 15/42; H04R 29/00
[52] U.S. Cl. .................................. 364/415; 364/571; 128/746; 73/585
[58] Field of Search ............... 364/415, 571; 73/585, 73/1 DV; 128/746; 381/25, 26, 60

[56] References Cited

U.S. PATENT DOCUMENTS

| | | | |
|---|---|---|---|
| 3,466,652 | 9/1969 | Heyser | 367/102 |
| 3,920,904 | 11/1975 | Blauert | 381/25 |
| 3,959,770 | 5/1976 | Schaefer | 367/13 |
| 4,107,465 | 8/1978 | Charlebois | 179/1 |
| 4,118,601 | 10/1978 | Yeap | 381/60 |
| 4,279,019 | 7/1981 | Heyser | 364/553 |
| 4,284,847 | 8/1981 | Besserman | 73/585 |
| 4,471,171 | 9/1984 | Kopke | 179/107 R |
| 4,489,610 | 12/1984 | Slavin | 128/746 |

*Primary Examiner*—Jerry Smith
*Assistant Examiner*—Gail Hayes
*Attorney, Agent, or Firm*—Jerry W. Mills; Gregory M. Howison

[57] ABSTRACT

An audiological analyzer includes a speaker (12) for generating soundwaves, which are generated by a test pattern generator (20). A frequency/level shaper (18) is disposed between the test pattern generator (20) and the speaker (12) for determining both the level and the frequency response of a given signal. A TDS/ETC analyzer (28) is connected to a transducer (34) which is disposed adjacent the ear (14) of a patient. The analyzer (28) allows for exact inplace measurement of the medium through which the soundwaves are transmitted. This information is stored in a memory (40) in the form of a calibration response curve. This data available in order to compensate for attenuation through the medium. This compensation ensures proper sound pressure level delivery to the ear (14). In addition, the frequency/level shaper (18) has equalizers (90) and (92) disposed therein for entering a predetermined response. This predetermined response represents the response of a corrective device such that the tests can be run again with the response for the corrected device adjusted for. In this manner, the patient can be tested without a device and with a simulated device.

20 Claims, 8 Drawing Figures

AUDIOLOGIC TESTING METHOD AND APPARATUS WITH COMPENSATING MEANS FOR SOUNDWAVE ATTENUATION THROUGH A TRANSMITTING MEDIUM

TECHNICAL FIELD OF THE INVENTION

The present invention pertains in general to the field of audiology and, more particularly, to a method and apparatus for accurately delivering a predetermined sound level to a remote point in an uncontrolled environment.

BACKGROUND OF THE INVENTION

In the field of audiology, it is necessary to deliver a predetermined sound level to a specific point. This point can be the pinna of the ear or the transducer surface of a hearing aid. Heretofore, the measurement of either a passive device such as the hearing aid or the response of the human ear has been accomplished by first calibrating a sound source to a predetermined point in a "sound booth" and then transmitting calibrated levels of sound to the unit under test or patient's ear. However, once the individual or the device is placed into the sound booth, the acoustics of that particular enclosure may change, thus changing the calibration.

To minimize calibration errors when testing a patient's hearing, headphones are normally used with the assumption that the distance from the headphone transducer to the external auditory canal is a constant. Once the headphones are in place, the patient can then provide an evoked response to various tone patterns that are supplied to the individual. However, as described above, the test system for obtaining the evoked response normally requires a set of calibrated headphones and a sound booth. When testing a patient's hearing in a "free field", calibration and control of sound pressure levels at the ear becomes more difficult. This is due to the fact that sound pressure varies as a function of the distance between the patient and the sound source.

In calibrating a system for either measuring a device such as a hearing aid or calibrating the sound pressure level (SPL) at a remote point such as the human ear, it is necessary to have both a precision transducer at the remote point and a knowledge of the loss and frequency response of the medium through which the sound wave is being transmitted. In addition, it is also necessary to minimize reflections from foreign objects proximate the remote point that may result in reflections which can set up interference patterns proximate the remote point. These interference patterns can severely detract from the accuracy of the measurement performed.

In order to simplify measurements at a given point, a measurement technique has been developed which produces a time delay spectrum. This is referred to as Time Delay Spectrometry (TDS) which is disclosed in U.S. Pat. No. 4,279,019. This technique utilizes a frequency generator disposed at one point termed the "source" and a sound transducer disposed at a remote test point. The frequency is generated for a very short duration of time and this frequency is sampled at a predetermined interval of time which is adjustable. The interval of time is equal to the delay which occurs as the sound passes through the transmission medium such as air. The sample is only taken for a short interval of time to prevent reflections from other boundaries proximate the remote test point from being summed with the sample taken. In this manner, it is possible to measure only the SPL that results from the transmitted frequency that is transmitted through the medium to the transducer at the remote point. Since propagation of sound through the medium undergoes some form of spherical spreading, the energy actually received at the remote test point is substantially attenuated with the remaining energy available for reflection off of different boundaries.

The above described TDS technique utilizes a swept frequency response and a narrow bandpass filter wherein the actual sweeping of a frequency source prevents any given frequency from being present for a long duration of time. The results provided by the TDS technique are a plot of SPL versus frequency. However, no information is provided regarding the reflections and the effect that they may have upon an evoked response test. This problem is addressed by another technique that has resulted from the original TDS technology and is disclosed in U.S. Pat. No. 4,279,019 issued to the same inventor. This technique provides an energy time curve for a given swept frequency response. In this technique, a "chirp" signal is output from the source and the Fast Fourier Transform of the received signal is taken. This provides the energy time curve (ETC) of the source signal. This ETC curve provides information regarding such things as reflections from other boundaries, etc.

Although the TDS technique and the ETC technique have been developed to aid in testing of devices in the various mediums without the reflections from objects within the medium interferring, the techniques at present are inadequate for application to the audiology industry since they are still time consuming at best. Therefore, there exists a need for a system which applies the concepts founds in TED and ETC to enhance testing of both the hearing response of an individual and the frequency response of a device such as a hearing aid.

SUMMARY OF THE INVENTION

The present invention disclosed and claimed herein comprises an apparatus for audiological testing which includes a signal generator for generating test signals and a source for receiving the test signals and generating soundwaves corresponding to those test signals. The attenuation of the test medium is measured between the source and a remote sense point as a function of frequency of the test signals. A calibration response curve is then generated which is comprised of deviation levels for each generated frequency of each of the test signals. The deviation is equal to the attenuation of the test medium for each frequency in the test signal range. The calibration response curve is stored in memory and is accessible by a processor. The processor controls the signal generator to generate the test signals in accordance with the predetermined pattern and also controls the level of these test signals in accordance with the calibration response curve such that a predetermined output level can be ensured at the patient's ear.

In another embodiment of the present invention, an equalizer is interposed between the signal generator and the source to provide an offset frequency response to the signal generated by the source. This offset response is independent of the compensation provided by the calibration response curve and allows the audiologist to insert a predetermined correction response into the testing system to simulate a corrective device such as a hearing aid. In this manner, the audiologist can first run a test to decide what type of corrective device is required and then simulate that test device to ensure that his decision is correct.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figures 1, 3:
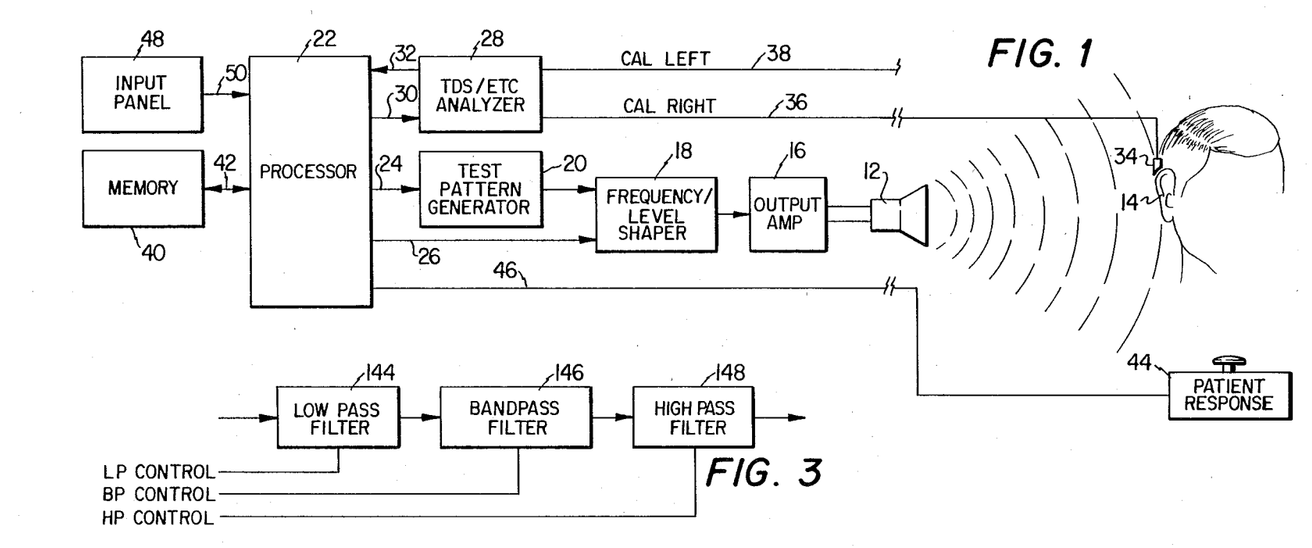
FIG. 1 illustrates a schematic block diagram of the evoked response system in accordance with the present invention.
FIG. 3 illustrates a schematic block diagram of the equalizer.

Referring now to FIG. 1, there is illustrated a block diagram of an evoked response system in accordance with the present invention. A sound source 12 is provided to generate soundwaves and the corresponding sound pressure to an individuals ear 14. The speaker 12 can be any type of transducer for generating soundwaves in a medium such as air and is connected to an output amplifier 16 for amplification of signals received from a frequency/level shaper 18. The frequency/level shaper 18 receives signals from a test pattern generator 20 and determines the frequency response thereof. The output is delivered to the output amplifier 16.

A processor 22 is provided which is connected to the test pattern generator 20 through a control line 24 and to the frequency/level shaper 18 through a control line 26. The processor 22 controls the functions of both the test pattern generator 20 and the frequency/level shaper 18 to produce sound at the output of the speaker 12 at a predetermined frequency or group of frequencies and at a predetermined sound pressure level.

An analyzer 28 is provided that performs both time delay spectrometry (TDS) and also generates an energy time curve (ETC). Hereinafter, the analyzer 28 will be referred to as a "TDS/ETC Analyzer". The TDS/ETC analyzer 28 is connected to the processor 22 through a control line 30 to receive control signals therefrom. The information output by the TDS/ETC analyzer 28 is input to the processor 22 through a data line 32. The operation of the TDS/ETC analyzer 28 is described in U.S. Pat. Nos. 3,466,652 issued on Sept. 9, 1969 and U.S. Pat. No. 4,279,019, issued on July 14, 1981, both of which are issued to R. C. Heyser and both of which are incorporated herein by reference.

The TDS/ETC analyzer 28 has two remote inputs, one connected to a remote transducer 34 through a signal line 36 labeled CAL RIGHT and a second transducer (not shown) which is connected through a signal line 38 and labeled CAL LEFT. The transducer 34 is disposed adjacent the pinna of the ear 14, preferably clipped onto the pinna proximate the external auditory canal. The transducer 34 is a precision device having a flat response curve over the frequency band of interest. However, as will be described hereinbelow, the processor 22 can compensate for the frequency response of the transducer 34.

In operation, the processor 22 controls the test pattern generator 20 to output a calibration signal configured as a "chirp" signal. The chirp signal is comprised of a test signal that is swept in frequency from a low frequency to a high frequency. The frequency is only swept one time for each signal such that energy is not being output by the test pattern generator 20 except during the signal sweep. This chirp signal can be repeated a number of times, depending upon the calibration tests performed. The frequency/level shaper 18 is controlled by the processor 22 to provide a flat frequency response to the test pattern generator 20 during generation of the chirp signal.

The chirp signal output during the calibration mode is detected by the precision transducer 34 on the pinna of the ear 14 and fed back to the input of the TDS/ETC analyzer 28. The TDS/ETC analyzer 28 receives the output of the transducer 34 and generates a "time window" which is synchronized with a predetermined delay and analyzes the SPL during this time window. The delay is a function of the medium through which sound is being transmitted and the distance between the speaker 12 and the transducer 34. The operation of the TDS/ETC analyzer in the calibration mode is taught in U.S. Pat. Nos. 3,466,652 and 4,279,019 which were incorporated herein by reference.

The signal output by the TDS/ETC analyzer 28 in the TDS mode is a plot of level versus frequency. In the preferred embodiment, the TDS/ETC analyzer 28 is a digital apparatus which samples the SPL corresponding to a given frequency and digitizes this level for storage in a memory 40 in association with the given frequency. The memory 40 is connected to the processor 22 through an address/data line 42.

Once the frequency response of the medium is known, the processor 22 is placed into the test mode. In this mode, the test pattern generator 20 is controlled to output various combinations of tones in accordance with conventional testing procedures for the audiology industry. For each tone output, the frequency/level shaper 18 is controlled to present attenuation or gain at that particular frequency to compensate for loss through the medium such that a predetermined SPL can be delivered to the ear 14. For example, if a reference SPL is established for a given electrical signal input to the speaker 12 at a frequency of 500 Hz and an SPL of 20 db, a signal at a predetermined level is input the to frequency/level shaper 18 and the gain or attenuation thereof adjusted to produce the appropriate level output by the speaker 12 that will result in an SPL of 20 db being present at the pinna of the ear 14. It should be understood that the speaker 12 can also be a factor in a frequency response of the medium, since only the electrical input signal to the speaker 12 is known. Therefore, the system of FIG. 1 can also compensate for the speaker frequency response.

The processor 22 in conjunction with the memory 40 has stored therein a "calibration response" that can be utilized for any given frequency to produce the appropriate SPL at the pinna of the ear 14. This calibration response is a countour or "curve" of the compensation required for each frequency output by the speaker 12. By adjusting the level of the test signals in accordance with the calibration response curve, the proper SPL can be delivered to the ear.

When the proper SPL is delivered to the individual or patient, the patient is allowed to provide an evoked response with a patient response device 44 which is connected to the processor 22 through a signal line 46. As the test progresses, the patient supplies the feedback to the system with the patient response device 44. When the test is completed, the responses provided by the patient are analyzed by the processor 22 or output to a remote device and analyzed by conventional methods. After analysis of the patient response, a determination of the appropriate correction measures can be made. These corrective measures are normally in the form of a hearing aid which provides the proper level of boost in the frequency response of the individuals hearing. After selection of an appropriate hearing aid the operator can then simulate the response of this hearing aid by making the appropriate adjustments to the frequency response of the frequency/level shaper 18. This allows the audiologist to determine if his selction is appropriate without having to actually fit the patient with a hearing aid. This is similar to the methods utilized by optomologists to determine if a given corrective lens will suit an individual. The data required to simulate the hearing aid can be input to an input panel 48 which is connected to the processor 22 through a data line 50.

For example, if a patient provides an evoked response which indicates the need for high frequency boost in his hearing response, it will be necessary to determine the type of hearing aid that is required for this patient. Since hearing aids are not infinitely adjustable and there are only a finite number to select from, the hearing aid having the most desirable frequency response will have its parameters input on the input panel 48 to the processor 22. The processor 22 then controls the frequency/level shaper 18 to provide a frequency response that has the correct amount of high frequency boost corresponding to that achievable by the selected hearing aid. Thereafter, the test is again run with the system of FIG. 1 to determine if the patient provides the correct evoked response. If so, the patient is then provided with this particular type of hearing aid. In this manner, an immediate feedback is provided to the audiologist to determine the specific hearing aid required by the patient, the type of hearing aid defined by a test rather than the actual use of the patient in every day life.

During each test of the system of FIG. 1, the calibration signal can be repeated prior to generating any test pattern or after a predetermined number of tests in the pattern. This may be necessary since an individual may move slightly, thereby changing the parameters of the medium between the speaker 12 and the pinna of the ear 14. This is an important aspect of the present invention in that the actual SPL delivered to the pinna of the ear 14 is a direct function of the attenuation of the medium and the distance from the ear 14 to the speaker 12. By allowing this type of calibration, a calibration response can be generated for each test tone output by the test pattern generator 20. In this manner, a higher degree of versitility is realized in performing audiological tests.

Figure 2:
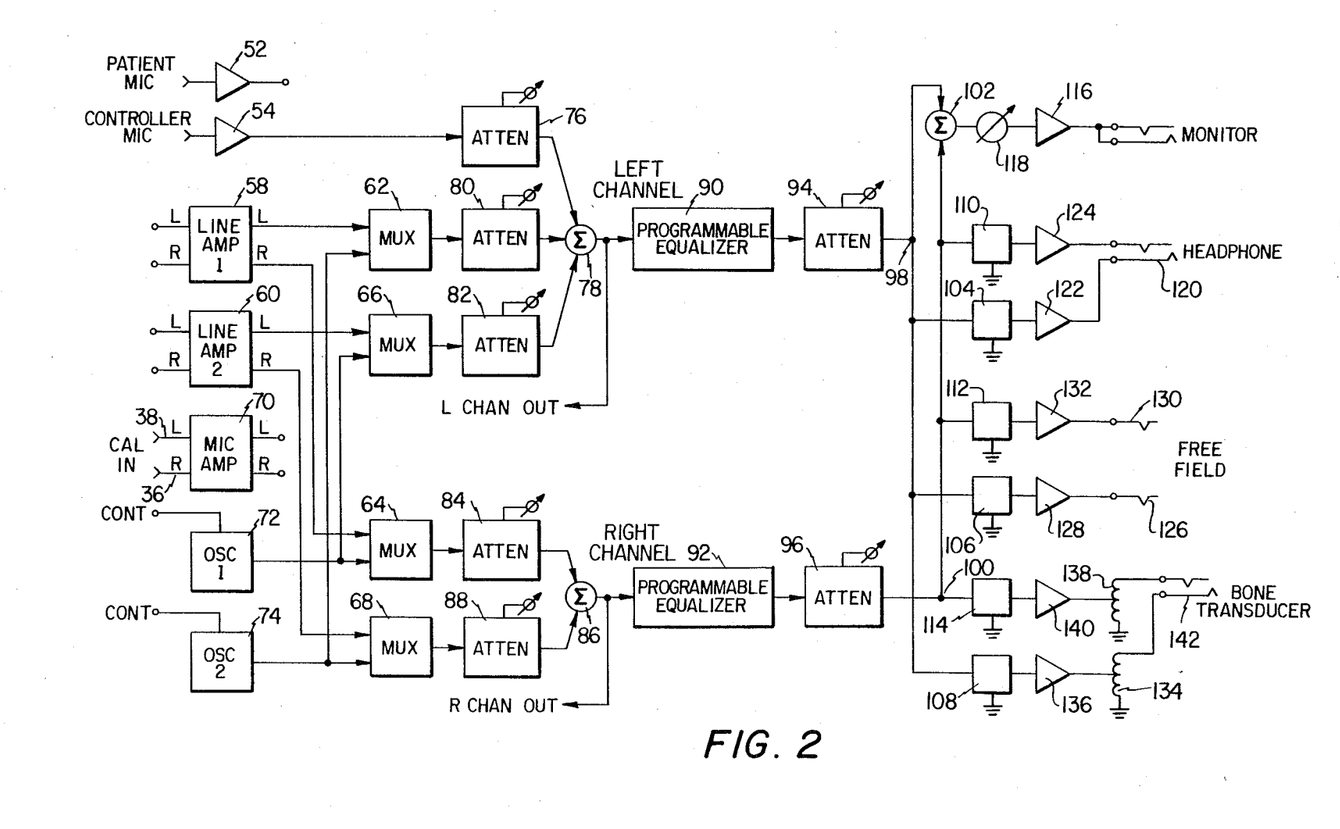
FIG. 2 illustrates a schematic diagram of the analyzer in accordance with the present invention.

Referring now to FIG. 2, there is illustrated a schematic block diagram of the output amplifier 16, frequency/level shaper 18 and the test pattern generator 20 of FIG. 1. Each of these circuits is divided into a left channel and a right channel to provide the ability for testing the right and left ear of the patient. There are a number of controls for generating the various sound patterns for input to the speaker 12. A microphone preamp 54 has the input thereof connected to two inputs of an attenuator 76 with the attenuation thereof being variable. A preamp 52 is also provided that has the output thereof connected to the processor 22. Although not shown, the processor 22 has an internal analog to digital (A/D) converter internal thereto to covert analog signals to digital signals for processing by the processor 22. The preamp 52 is connected to a patient microphone and the input of the preamp 54 is connected to a controller microphone. The patient microphone is a microphone that is accessible by the patient to reply directly to the audiologist that is running the test whereas the controller mike is for use by the audiologist to converse with the patient.

A dual line amplifier 58 and a dual line amplifier 60 each have a left and right input thereto. Each of the left and right inputs thereof are individually amplified and output on left and right outputs. The line amplifiers 58 and 60 are labeled "#1" and "#2" and are high impedance dual amplifiers for use with auxiliary devices that may be connected thereto. The left input of the line amplifier 58 is connected to one input of a multiplexer 62 and the right input thereof is connected to one input of a multiplexer 64. The left input of the line amplifier 60 is connected to one input of a multiplexer 66 and the right input thereof is connected to one input of a multiplexer 68.

A dual microphone preamplifier 70 has two inputs for receiving the inputs from the transducer 34 attached to the pinna of the ear 14 and to the transducer connected or placed proximate to the right ear (not shown). The dual preamplifier 70 has an individual amplifier for each of the inputs to supply left and right outputs therefrom. These outputs are also connected to the input of the processor 22 for processing by the A/D converter internal thereto.

A first oscillator 72 is labeled "OSC-1" and is controlled by the processor 22 to receive a digital signal and generate a frequency in response thereto. The output of the oscillator 72 is connected to one input of the multiplexer 64 and also to one input of the multiplexer 66. An oscillator 74 is labeled "OSC-2" and has the output thereof connected to one input of the multiplexer 62 and one input of the multiplexer 68. The oscillators 72 and 74 both receive a digital input signal from the processor 22 to enable the predetermined signals to be output at a given frequency or pattern of frequencies, depending upon the digital signal supplied by the processor 22. The multiplexers 68 and 62 select the output of the oscillator 74 and determine which of the right or left channels that it is routed to, whereas the multiplexers 64 and 66 select the output of the oscillator 72 and determine which of the channels that it is routed to. The oscillators 74 and 72 are utilized in both the testing mode of the system of FIG. 1 and also in the calibrate mode.

The output of a variable attenuator 76 is connected to the input of the summing junction 78 on the left channel. The multiplexer 62 has the output thereof connected to the input of a variable attenuator 80, the output of which is connected to the summing junction 78. The multiplexer 66 has the output thereof connected to an input of the variable attenuator 82, the output of which is connected to the summing junction 78. The multiplexer 64 has the output thereof connected to the input of an attenuator 84, the output of which is connected to a summing junction 86 on the right channel.

The multiplexer 68 has the output thereof connected to the input of an attenuator 88, the output of which is connected to the input of the summing junction 86. The summing junction 78 sums the signals of the output of the attenuators 76, 80 and 82 whereas the summing junction 86 sums the outputs of the attenuators 84 and 88.

The output of the summing junction 78 is input to a programmable equalizer 90 and the output of the summing junction 86 is input to a programmable equalizer 92. The output of the programmable equalizer 90 is connected to the input of a variable attenuator 94 and the output of the programmable equalizer 92 is connected to the input of a variable attenuator 96.

The output of the variable attenuator 94 is connected to a node 98 and the output of the attenuator 96 is connected to a node 100. The node 98 is connected to one input of a summing junction 102 and the inputs of analog switches 104, 106 and 108. The node 100 is connected to the other input of the summing junction 102 and the inputs of analog switches 110, 112 and 114. The output of the summing junction 102 is connected to the input of an amplifier 116 through a volume control 118. The output of the amplifier 116 drives a headphone jack labeled "Monitor". The output of the switch 104 is connected to one terminal of a headphone jack 120 through an amplifier 122 and the output of the switch 110 is connected to the other terminal of the headphone jack 120 through an amplifier 124. The headphone jack 120 is labeled "Headphone".

The switch 106 is connected to an output jack 126 through an amplifier 128 and the switch 112 is connected to an output jack 130 through an amplifier 132. The output jacks 126 and 130 are labeled "Free Field". This represents separate speakers in an open environment. The switch 108 is connected to the input of a transformer 134 through an amplifier 136 and the switch 114 is connected to the input of a transformer 138 through an amplifier 140. The transformer 138 and the transformer 134 are each connected to one terminal of a bone transducer 142 which is labeled "Bone Transducer". The bone transducer output jack 142 is utilized for connection to bone transducers of the type that are interfaced with the mastoid bone for individuals with defective eardrums and the such. The analog switches 104, 106, 108, 110, 112 and 114 are controlled by processor 22 such that they are software controlled.

In operation, the attenuators 76, 80, 82, 84 and 88 are operable to provide approximately 60 db of attenuation and the attenuators 94 and 96 are also individually able to provide 60 db of attenuation. The attenuators are controlled by the processor 22 through digital signals supplied thereto to provide the attenuation in various increments, depending upon the particular type of attenuator utilized. In operation, the attenuator 94 operates in conjunction with one of the attenuators 76, 80 or 82 attached to the input of the summing junction 78 to provide a total of 120 db of attenuation. In a similar manner, the attenuator 96 operates in conjunction with the attenuators 84 and 88 through the summing junction 86 to provide 120 db of attenuation.

There are two modes of operation for the circuit of FIG. 2. In the first mode, a signal is generated by either the oscillators 72 or 74 or external units input through the line amps 58 and 60. For simplicity purposes, only the tests performed on the right channel will be described. In the first mode, a test is performed with the programmable equalizer 92 set to have a flat response. In this mode, a series of tones having a predetermined signal output level are generated by, for example, the oscillator 72 that is selected by the multiplexer 64. The attenuators 84 and 96 are set to a level that is determined by the SPL that is to be delivered to the ear as a function of the calibration response stored in memory 40. A simple example would involve a generation of a single tone at a predetermined frequency by the oscillator 72 with the attenuators 84 and 96 adjusting the level to provide a predetermined SPL in accordance with the calibration response stored in memory 40. The tone would be output on either the headphone jack 120 or the free field jack 130 for a predetermined interval of time. The system then waits for a predetermined interval of time to determine if a patient response has been received from the patient response indicator 44. The presence or absence of a response is then stored and the next tone of the sequence output by the oscillator 72 at either the same frequency or a different frequency, depending upon the particular test sequence being performed. This sequence is completely stepped through and the patient response is recorded.

After this sample test has been performed, the audiologist can analyze this data to make a determination of whether corrective measures must be taken. If the determination is made that a device such as a hearing aid is required, the response of the hearing aid can be programmed into the equalizer 92. For example, a patient may require high frequency boost and an appropriate hearing aid can be selected, which response can be preprogrammed into memory 40. It is then only necessary for the audiologist to select the best response for input to the equalizer 92. However, the equalizer 92 may be a manual equalizer with separate settings for each filter section therein.

Once the response for a given hearing aid is selected and input to the equalizer 92, the identical test that determined the need for the particular hearing aid is then rerun. In this manner, immediate feedback is provided to the audiologist as to whether the selected hearing aid will provide the necessary hearing correction for the patient. This is necessary since in some situations there is a fault in the test rather than in the hearing of the individual and an immediate correction will determine if it is a hearing defect as opposed to a testing problem.

Referring now to FIG. 3, there is illustrated a schematic block diagram of the programmable equalizers 90 and 92 of FIG. 2. The input to the programmable equalizer is first input to a programmable low pass filter 144 which has the break points thereof programmable. The output of the low pass filter is input to a band pass filter bank 146 which is comprised of six active band pass filters that can provide either attenuation or gain. The gain or attenuation provided by each of the filters in the bank 146 are controlled by the processor 22. The output of the band pass filter bank 146 is input to a programmable high pass filter 148, the break points of which are programmable. The output of the high pass filter is connected to the input to one of the respective attenuators 94 or 96.

The low pass filter 144 is connected to the processor 22 through a control input labeled "LP Control", the band pass filter bank 146 is connected to the processor 22 through a control line labeled "BP Control" and the high pass filter 148 is connected to the processor 128 through a control line labeled "HP Control". The break points of the various filters are arranged in one-third octave segments. In the preferred embodiment, the break points of the low pass filter 144 are programmable in one-third octave steps from 100 Hz to 500 Hz. For example, the first break point is set at 100 Hz and rolls off at 3 db per octave. The second selectable break point is set at 125 Hz with the next third octave step being 160 Hz. This continues up to 500 Hz. Depending upon the break point selected, the low pass filter will have the 3 db break point set at that frequency and the skirt for the low pass filter 144 will roll off at 3 db per octave from that break point.

The high pass filter 148 is similar to the low pass filter 144 with the exception that its break points are set in one-third octave steps for a frequency of 2500 Hz to a frequency of 10,000 Hz. For example, the first break point can be set at a frequency of 2500 Hz with the next one-third octave break point being set at 3150 Hz. The high pass filter 148 utilizes a third order Butterworth filter that rolls off at 3 db per octave in the skirt thereof. By selecting the appropriate break point, the high end response of the equalizer can be determined.

The band pass filter bank 146 is designed with six separate band pass filters spaced evenly apart in the band pass section from 630 Hz to 2000 Hz and each having a one-third octave bandwidth. Therefore, the first band pass filter occupies the frequency range of 500 to 630 Hz, the second a bandwidth of 630 to 800 Hz, etc. The filters are cascaded and the responses adjusted such that at zero gain, the response thereof is flat. By selectively increasing the gain of one of the band pass filters, a given degree of "boost" can be provided at that given frequency.

Although a programmable equalizer has been disclosed in FIG. 3, it should be understood that a manual equalizer can be utilized in place of the programmable equalizers 90 and 92 of FIG. 2. It is only necessary to be able to provide a flat frequency response in the initial test mode and calibration mode and then input the response of a given hearing aid or some such corrective device. However, it is also possible to custom fit a response to a patient's hearing defect and then fabricate a correction device that realizes this frequency response, such that the appropriate correction can be made to the hearing of the patient.

Figure 4:
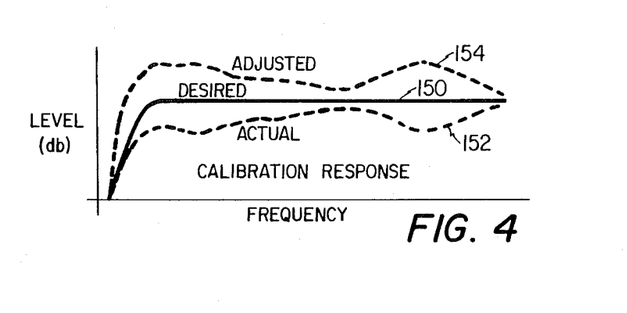
FIG. 4 illustrates a frequency response illustrating the calibration procedure.

Referring now to FIG. 4, there is illustrated a representative graph of frequency versus level for determining the calibration response. In performing a test, it is desirable over a given frequency range to provide a predetermined SPL to a remote point, such as the transducer 34 in FIG. 1. This is represented by a curve 150. However, due to attenuation experienced in a given medium and the response of a given speaker or transducer at the source, this desired response curve 150 is not obtainable by driving the source transducer with a constant input signal. Rather, some correction must be made and this correction is one of the primary objects of the present invention.

The actual SPL received at the remote point for a constant driving signal at the source is represented by a curve 152. As illustrated, this curve is erratic as a function of frequency. In order to obtain a predetermined reference, it is necessary to determine the actual deviation between the desired curve 150 and the actual curve 152 for each frequency generated and stored as deviation in the memory 40. This results in a contour 154 that represents the deviation from the desired curve 150 which must be added to the actual curve 152 to achieve the desired curve 150.

The deviation of the actual curve 152 in db from the desired curve 150 is stored in the memory 40 for each frequency measured. Therefore, a desired SPL at a given frequency would have a corresponding level stored in memory. This would be fetched from memory and applied to one of the oscillators to generate the appropriate level output from the speaker 12. For example, if a level of 20 db were desired at the ear 14, it would be necessary to apply a certain signal output from the oscillator. In the ideal situation, a 20 db SPL at the ear 14 would correspond to a predetermined level output from the oscillator. However, due to the distance traveled and the attenuation resulting from the particular medium in which the sound is transmitted, an adjustment would have to be made. This adjustment is that stored in the memory 40 as the calibration response. One calibration point corresponding to the transmitted frequency would be retrieved from memory and the signal level of the oscillator adjusted to output the correct SPL. This can be done for each frequency generated.

Figure 5:
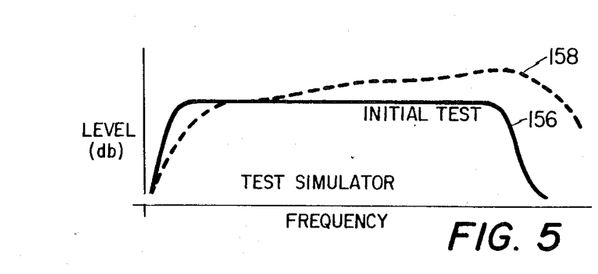
FIG. 5 illustrates a frequency response for the test simulation mode.

Referring now to FIG. 5, there is illustrated a graph of frequency versus level for the test simulation. In the initial test mode, the frequency response of the equalizers 90 and 92 is flat, as represented by a frequency response curve 156. However, after the audiologist has examined the results and determined the type of corrective measures needed, a hearing aid or some similar corrective device can be selected. The response for this corrective device can then be programmed into the equalizers 90 or 92, resulting in a response curve 158, as illustrated by dotted lines. As illustrated, this response curve has a decreased low frequency response and increased or "boosted" high frequency response. This is facilitated by increasing the frequency at the break point for the low pass filter portion of the equalizers and also increasing the break points for the high pass filter thereof. Additionally, the gain of the various band pass filters in the band pass filter section are increased to provide boost.

After the response curve has been corrected with the equalizers 90 and 92, the test is then run again to determine if this corrected frequency response evokes a correct response to the given test. It is important that the audiologist have an immediate feedback as to the results of the tests with and without the corrective response. In this manner, the audiologist can make a more accurate determination as to the validity of the test and his choice of a corrective device.

Figure 6:
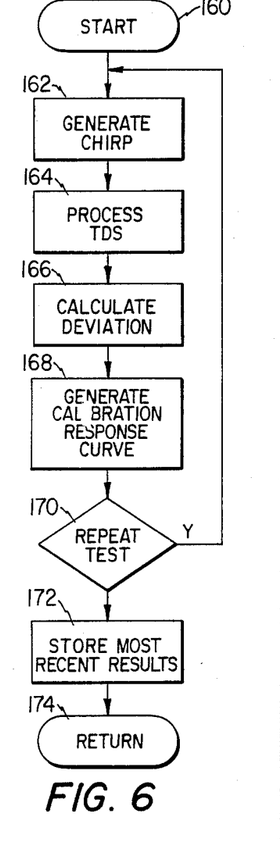
FIG. 6 illustrates a flow chart of the calibration procedure.

Referring now to FIG. 6, there is illustrated a flow chart for the calibration procedure with the processor 22. The program is initiated with a start block 160 and then flows to a function block 162 which indicates the step by which a chirp signal is generated from the test pattern generator 20 in response to the TDS/ETC analyzer 28. This chirp signal is output by the speaker 12 and received by the transducer 34. The program then flows to a function block 164 to process the signal with the TDS/ETC analyzer 28 and determine the amount of time delay and the relative amplitude of the SPL received at the transducer 34. This is done in conjunction with the processor 22 since the characteristics of the transducer 34 may have to be compensated for.

After the relative amplitude as a function of frequency has been measured, the program flows to a function block 166 to calculate the deviation as a function of frequency with respect to the desired response at the transducer 34. The program then flows to a function block 168 in which the calibration response curve is generated, as illustrated in FIG. 4 with respect to curve 154. The program then flows to a decision block 170 to determine whether the test is repeated. For some applications, it may be necessary to repeat the test a number of times and compare the results such that a final calibration response curve is generated only when the results can be repeated. If the test is to be repeated, the program flows along the "Y" path back to the input of the function block 162 and, if the test is not to be repeated, it flows along the "N" path thereof to a function block 172. The function block 172 indicates the step at which the results are stored in the memory as a function of frequency. The function block then flows to a return block 174 to return to the main program.

Figure 7:
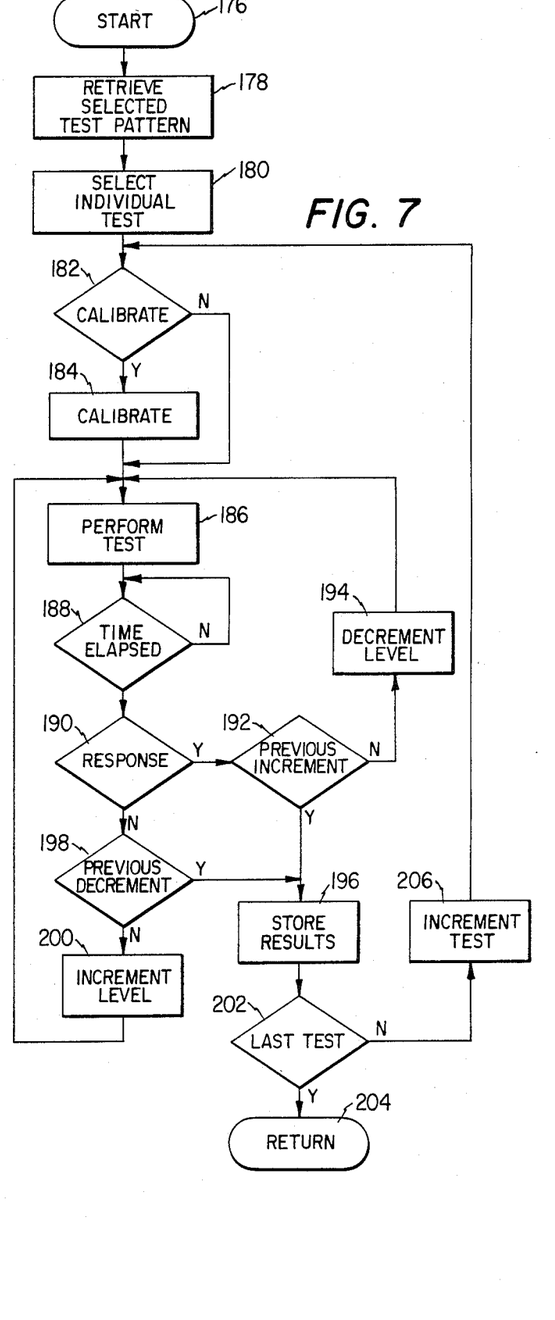
FIG. 7 illustrates a flow chart of the test procedure.

Referring now to FIG. 7, there is illustrated a flow chart for the test mode program, which is initiated at a start block 176. The program then flows to a function block 178 to retrieve a selected test pattern. This selected test pattern may be input on the input panel 48 or it may be prestored in memory 40. If it is prestored, it is only necessary to indicate which test pattern is to be provided to the patient and this test pattern retrieved from memory.

After selection of the test pattern, the individual test in the sequence of tests is then selected, as indicated by a function block 180. After selection of the single test, the program flows to a decision block 182 to determine if the system is to be calibrated after each test. If it is to be calibrated, the program flows along the "Y" path thereof to a function block 184 indicating the calibration subroutine of FIG. 6 and then to a function block 186 to perform the test. If, however, the system is not to be calibrated, the program flows along the "N" path thereof to the input of the function block 186 to bypass the calibration step of function block 184. In some situations, it may be necessary to perform a calibration test immediately prior to each test tone generated or test performed to ensure that the patient has not moved, such that distance between the source and the remote test point has not changed. In this manner, a correct SPL can be ensured at the patient's ear.

After the test has been performed, the program flows to a decision block 188 to determine if a predetermined duration of time has elapsed. This is essentially a software time delay which forces the program to flow along the "N" path thereof back to the input of the decision block 188 until a certain number of program delay steps have been performed. After performance of this, the program then determines whether a response has been evoked from the patient.

After the predetermined duration of time has elapsed, the program flows to the input of a decision block 190 to determine if a response has been evoked from the patient. If a response has been evoked, the program flows along the "Y" path thereof to a decision block 192 to determine if there has been a previous increment of the sound level. In performing the test, it is necessary to determine the threshold of hearing. In order to effect this test, a "Yes" response will require the level to be lowered and the test performed again until a "No" response is evoked. A "No" response is essentially lack of response. Alternatively, lack of a response will result in incrementing the level until a "Yes" response is received. This decision is made by the decision block 192.

If a previous increment has not been made, the program flows to a function block 194 to decrement the level and then returns to the input of the function block 186 to perform the test again. However, if there was a previous increment indicating a previous lack of response, the program flows along the "Y" path thereof to a function block 196 to store the results. This indicates that the threshold has been determined.

If the decision made by the decision block 190 is a lack of response, the program flows along the "N" path thereof to a decision block 198 to determine if there was a previous decrement or a previous response. If there had been a previous response, this would indicate that the program had proceeded along the "Y" path from the decision block 190 and the level decremented. If there was a previous decrement, the program flows along the "Y" path from the decision block 198 to the input of the function block 196 to store the results in memory 40.

If there has not been a previous decrement, indicating that there was no previous response, the program flows along the "N" path thereof to a function block 200 indicating the step by which the level is incremented and then the program flows back to the input of the function block 186 to preform the test at this new level. The program will flow to the function block 200 until a "Yes" response has been evoked, at which time it will flow through the decision block 192 to the function block 196.

After the results have been stored in the step indicated in the function block 196, the program flows to a decision block 202 to determine if this is the last test in the pattern. If it is, the program flows along the "Y" path thereof to a return block 204. If, however, it is not the last test, the program flows along the "N" path thereof to a function block 206 to increment the test and then back to the input of the decision block 182 and then the next test is performed.

Figure 8:
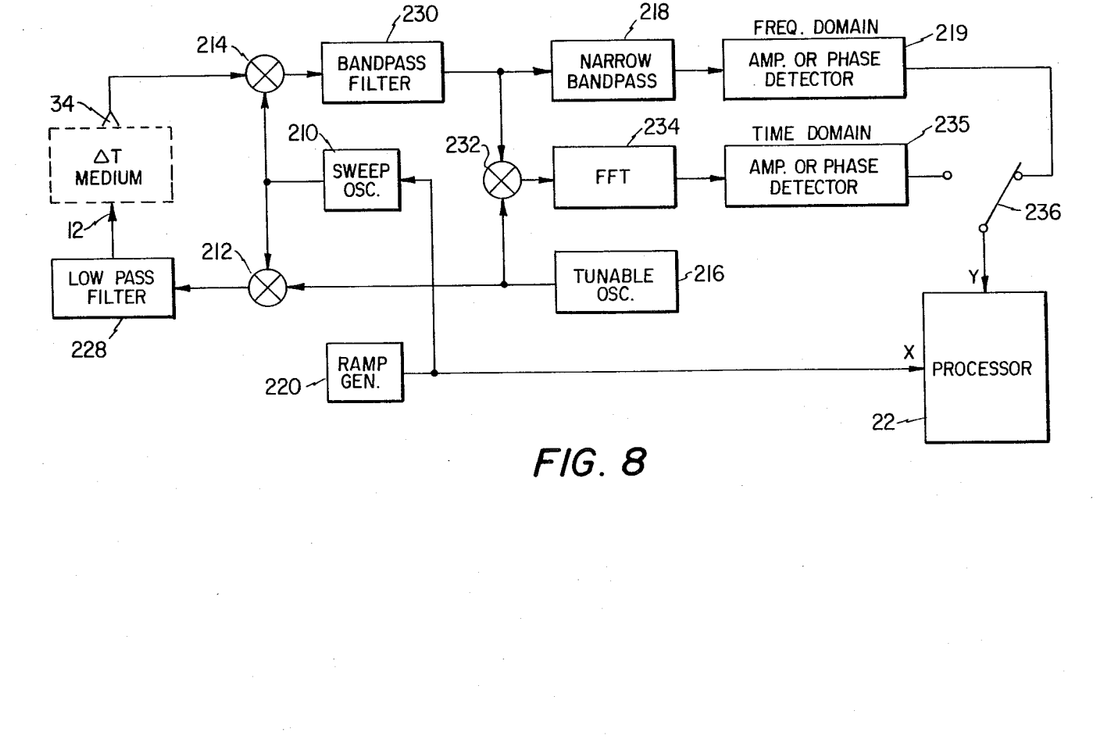
FIG. 8 illustrates a schematic diagram of the prior art TDS/ETC method.

Referring now to FIG. 8, there is illustrated a schematic block diagram of a time delay spectrometer (TDS) of the basic configuration disclosed in U.S. Pat. No. 4,279,019. The basic TDS is comprised of a precision sweep oscillator 210, mixers 212 and 224, a tunable oscillator 216 and a narrow band pass filter 218. A ramp generator 220 produces a voltage signal having a constant slope to sweep the oscillator 210, and to provide a horizontal output for the processor 22 for storage of the time delay spectrum of energy transmitted from the speaker 12 through medium with some fixed delay ΔT to the receiving transducer 34. However, it should be understood that any type of transmitter may be utilized and any type of receiver may be utilized when any other type of energy wave transmission through the medium. The sweep oscillator 210 and the ramp generator 220 are synonomous with the oscillators 72 and 74 but, for illustrative purposes, are shown separate.

The output of the sweep oscillator is delivered to the mixer 212 where it is modulated by the output of the tunable oscillator which produces an offset frequency. The modulation process in the mixer produces the sum and difference of the signals thus mixed. A filter 228 passes only the difference for transmission. At the receiver, the mixer 214 receives the sweep frequency for modulation with the received signal. The sum and difference frequencies are then transmitted through a band pass filter 230 and either the sum or difference is transmitted through the narrow band pass filter 218 as the information to be input to the processor 22. The tunable oscillator permits the time delay spectrometer to look at the transmitted signal which passes through different paths in the medium and is therefore subject to different delays. To see what signal modification is produced by a particular path of some time delay, the tunable oscillator is adjusted. That effectively displaces the spectrum displayed in time.

The output of the tunable oscillator is applied to a mixer 232 which effectively cancels the offset to produce a signal for processing through a Fast Fourier Transform (FET) circuit 234 that produces a signal representative of total energy as a function of time for storage in the memory 40 as an energy-time curve (ETC). A switch 236 is provided to selectively input the amplitude, or phase, of the output of the FFT or the output of the narrow band pass filter 218. The switch 236 is under software control and can be any type of electronic analog switch. The choice of amplitude or phase is made in the design of detectors 219 and 235. While the switch is in the position shown, data in the frequency domain is stored as TDS data and, while in the alternate position, data in the time domain is stored as ETC data.

It should be noted that a filter is not required to select one of the two frequencies (sum or difference) out of the mixer 232 because the FFT will, in the course of processing the signals, make the selection. Virtually any commercially available FFT may be used. It is assumed that the input section includes an analog to digital converter for digital processing, and the output section includes a digital to analog converter. If an FFT is selected without these analog to digital and digital to analog converters, it would be a simple task to provide the converters synchronized to operate with the FFT.

The device of FIG. 1 provides both a TDS and an ETC curve for storage in memory 40. By utilizing the TDS, the calibration response curve can be calculated and stored, as described above with reference to FIGS. 1-7. However, it may be desirable to determine information such as reflections from objects disposed about the patient or the remote test point. In this manner, the audiologist will be provided the information regarding possible errors to the testing procedure.

In summary, there has been provided a system for calibrating a radiating source and a medium through which that source propagates. The system includes a centralized computer which utilizes TDS techniques to determine the response at a remote point as a function of frequency. This response is then entered into a processor and a calibration response curve generated and stored in memory. This calibration response curve is available for later testing to compensate signal levels at the source such that the proper SPL is delivered to the remote point. This enables a test pattern to be run to generate various test tones or combinations of test tones for reception at the remote point by a patient. After processing of a given testing pattern, the processor then allows for compensation thereto to enter the response of a given correction device. The test patterns can then be run again with the correction response entered thereto such that the effectiveness of a correction device can be examined with respect to the patient.

Although the preferred embodiment has been described in detail, it should be understood that various changes, substitutions and alterations can be made therein without departing from the spirit and scope of the invention as defined by the appended claims.

What is claimed is:

1. An apparatus for audiological testing, comprising:
   signal generator means for generating test signals;
   source means for receiving said test signals and generating soundwaves corresponding to said test signals;
   means for measuring the attenuation of a testing medium between said source means and a remote sense point as a function of frequency of said test signals
   means for generating a calibration response curve, said calibration response curve comprised of deviation levels for each generated frequency of each of said test signals, said deviation being equal to the attenuation of said test medium;
   means for storing said calibration response curve;
   level means for varying the level of the generated soundwaves generated by said source means; and
   processor means for controlling said signal generator means to generate said test signals in accordance with a predetermined pattern and controlling said level means to adjust the level of said soundwaves output by said source means in accordance with said stored calibration response curve such that a compensated sound pressure level can be delivered to said sense point.

2. The apparatus of claim 1, wherein said signal generator means comprises a variable frequency oscillator.

3. The apparatus of claim 1 wherein said source means comprises a sound transducer for receiving the output of said signal generator means and generating soundwaves corresponding thereto.

4. The apparatus of claim 1 wherein said means for varying the level of the generated soundwaves comprises a variable attenuator disposed between said signal generator means and said source means and controlled by said processor means to vary the attenuation thereof.

5. The apparatus of claim 1 wherein said measuring means comprises:
   a transducer disposed at said remote sense point;
   a time delay spectrometer for receiving the output of said transducer;
   said time delay spectrometer operable through said processor means to control said signal generator means to generate a frequency having a swept response; and
   said time delay spectrometer sampling said transmitted swept signal at said remote sense point with said transducer in a time window to reduce reflections generated by the surrounding environment in accordance with time delay spectrometry techniques.

6. The apparatus of claim 1 and further comprising means for interposing an offset frequency response between said signal generator means and said source means such that the frequency response therebetween has a correction factor superimposed thereon that is independent of said calibration response curve.

7. The apparatus of claim 6 wherein said correction means comprises a frequency equalizer and a predetermined correction pattern input to said equalizer.

8. The apparatus of claim 7 wherein said correcton pattern is stored in said storage means.

9. The apparatus of claim 1 wherein said predetermined pattern is stored in said storage means.

10. An apparatus for audiological testing of a patient, comprising:
   a signal generator for generating test signals;
   variable attenuator means for receiving said test signals and varying the level thereof;

transducer means for receiving the output of said attenuator means and converting said attenuated test signals to soundwaves for transmission through a test medium;

a receiving transducer disposed proximate the ear of a patient for receiving said transmitted soundwaves;

a time delay spectrometer for controlling said signal generator to generate a chirp signal and measure frequency response of the received chirp signal at said receiving transducer to determine the variation of level as a function of frequency and the transmission medium in accordance with time delay spectrometry techniques;

means for generating a calibration response curve, said calibration response curve comprised of deviation levels for each generated frequency of each of said test signals, said deviation being equal to the attenuation of said test medium for each frequency;

means for storing said calibration response curve;

means for storing a predetermined test pattern, said test pattern defining said test signals to be generated and the sequence thereof; and a processor for controlling said signal generator means and said attenuator means to output said test signals in accordance with said predetermined pattern and said calibration response curve, the frequency of said test signals determined by said predetermined pattern and the level of said test signals determined by said predetermined pattern in combination with said stored calibration response curve such that the desired sound pressure level is delivered to the ear of the patient.

11. The apparatus of claim 10 wherein said signal generator generates fundamental frequencies and is digitally controlled by said processor, said processor outputting digital signals for control of said signal generator.

12. The apparatus of claim 10 wherein said signal generator generates two simultaneous test signals such that separate test signals can be supplied to either ear of said patient.

13. The apparatus of claim 10 wherein said transducer means comprises a speaker disposed in the free field.

14. The apparatus of claim 10 wherein said variable attenuator means comprises a variable attenuator having a digital control therefor, said processor providing digital signals for control thereof.

15. The apparatus of claim 10 and further comprising correction means disposed between said attenuator means and said transducer means for selectively altering the frequency response of the output soundwaves when said soundwaves are generated in accordance with said predetermined pattern and said calibration response curve, said correction means presenting a flat response curve when said time delay spectrometer is generating said swept frequency response.

16. The apparatus of claim 15 wherein said correction means comprises an equalizer for providing a selected frequency response.

17. The apparatus of claim 16 wherein said equalizer is programmable in accordance with predetermined correction data input thereto, said correction data accessible by said processor and said equalizer controlled by said processor.

18. A method for audiological testing of a patient, comprising:
generating test signals;
receiving the test signals and generating soundwaves corresponding to the test signals;
measuring the attenuation of a testing medium between the source and a remote sense point as a function of the frequency of the test signals;
generating a calibration response curve, the calibration response curve comprised of deviation levels for each generated frequency of each of the test signals, the deviation being equal to the attenuation of the test medium;
storing the calibration response curve;
controlling the generation of the test signals to generate the test signals in accordance with a predetermined pattern and varying the level of the generated test signals in accordance with the predetermined pattern and the calibration response curves such that a compensated sound pressure level can be delivered to the remote sense point, the remote sense point being adjacent the ear of the patient.

19. The method of claim 18 and further comprising receiving responses from the patient and storing the responses as a function of the test signals generated in accordance with the predetermined test pattern.

20. The method of claim 19 and further comprising providing a corrected response curve to the soundwaves transmitted in the test medium in accordance with the response data by the patient.

* * * * *